Jan. 15, 1935. J. J. GRULLEMANS Plant Pat. 118
PHLOX
Filed Aug. 31, 1934
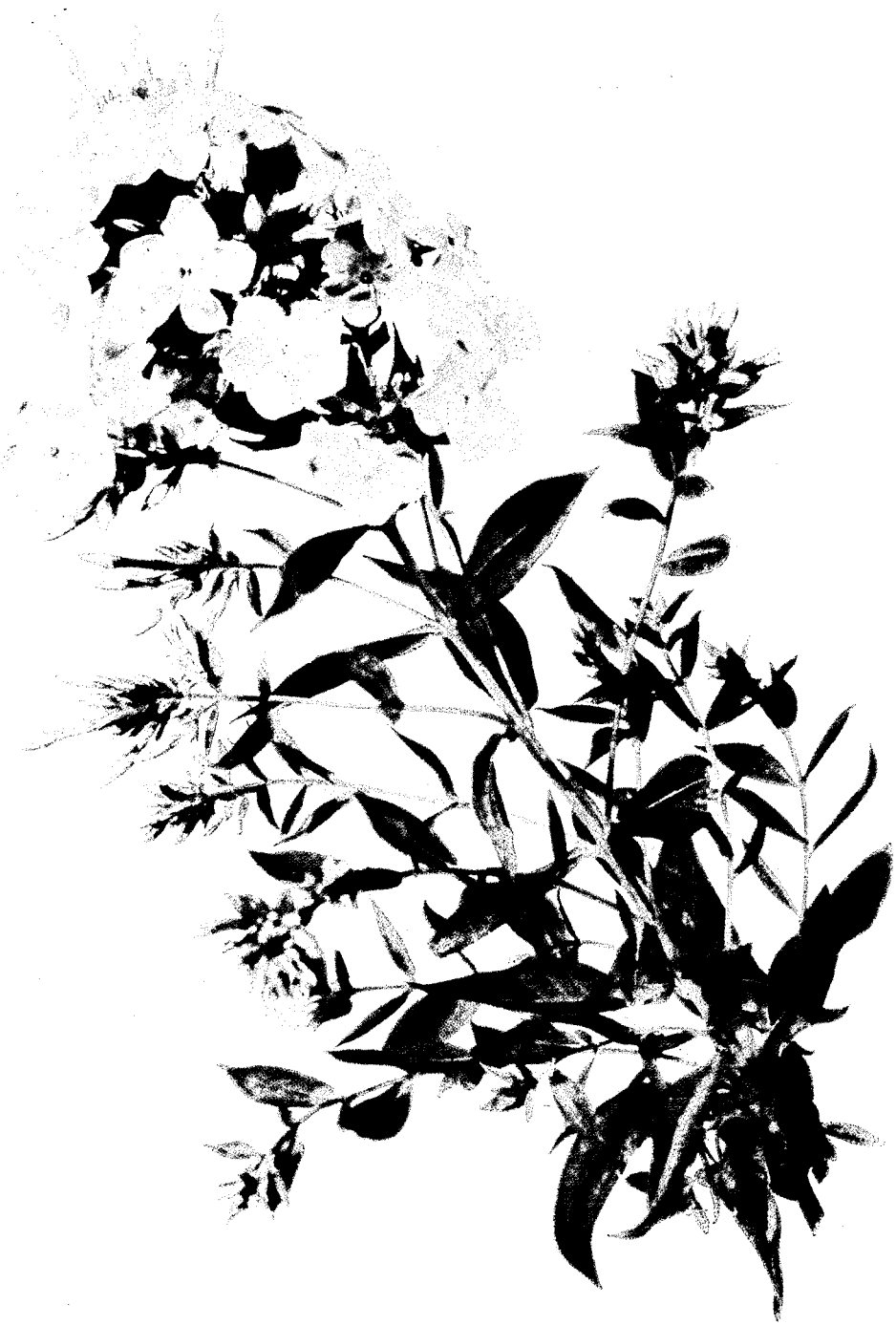
Inventor:
John J. Grullemans
By Justus W. Macklin
Atty Patented Jan. 15, 1935

Plant Pat. 118

UNITED STATES PATENT OFFICE

118

PHLOX

John J. Grullemans, Painesville, Ohio, assignor to The Wayside Gardens Company, Mentor, Ohio, a corporation of Ohio Application August 31, 1934, Serial No. 742,275

1 Claim. (Cl. 47—60)

The present invention relates to a novel and distinct variety of phlox of the general variety or genus of which "Elizabeth Campbell" and "Thor" types of blooming phlox are examples, but which has the following highly desirable characteristics:—namely a large number of secondary bloom heads besides the main flower head, whereby each plant blooms for a longer period; the bloom heads being upon laterals extending almost from the ground to the uppermost bloom head; and which grow and flower with unusual vigor; further also having rich full, dark green foliage, the flower spikes being produced in great abundance; and having a very fragrant odor. My new phlox is being grown in large quantities.

As to color, this new phlox blossoms in much richer and clearer shades of sparkling, iridescent pink than the Elizabeth Campbell phlox and does not have the dark flat salmon pink shading for which the Thor is noted. The flowers seen en masse leave one with the impression of a pure pastel pink of rare beauty never before encountered in hardy phlox. The bloom spikes or bloom heads growing at short distances apart along the stem, give a much more colorful shading, in full ensemble. This particular plant has blooms on each stem many times in number over those of previous phlox, and produces an abundance of this decorative color in garden effects, not heretofore obtainable for this character of flower.

My new phlox is reproduced by root cuttings or divisions and by which its characteristics above mentioned are faithfully reproduced. I have found that this may be done on a commercial scale and economically. Reproduction from seeds produces an entirely different plant, losing entirely the above characteristics and color, wherefore the plant herein shown, described and claimed may be reproduced asexually, only.

It will be noted that the leaves springing in pairs below the main or top flower head are of rich green color and from substantially the same point on the stem spring the flower spikes which are thus produced in great abundance. The drawing is an accurate reproduction of an early plant. Later plants have even more profuse abundance of flower spikes and larger flower heads than that shown in the drawing, and in which the lateral flower branches literally grow from this plant from the ground up. The plant is of medium growth and height and its continuation of bloom is a very marked characteristic in that it blooms over a very much longer period than phlox having merely a bloom head at the top of the stem.

My new phlox is largely a discovery. A plant of this nature apparently springing from a chance seedling came to my attention during the month of June, 1931, and by cultivation and asexually reproducing and propagating these plants, I have been able to uniformly reproduce this phlox on a large scale.

The drawing shows my phlox in its natural colors as nearly as possible to produce artificially, and from inspection of the drawing (the drawing was made originally photographically from an actual plant whereby it is an accurate reproduction of the foliage), it will be noted that bloom spikes below the head have not yet reached full bloom but they are in progressively advanced stages of growth and bloom from the lower part of the stem to the blooming upper portion or top thereof.

Having now fully shown and described my new phlox and the method of reproducing the same, what I claim and desire to secure by Letters Patent of the United States is:—

A phlox as herein shown and described, and characterized and distinguished by rich dark green foliage, great abundance of flower spikes or bloom heads, and blossoms of a rich pastel pink color.

JOHN J. GRULLEMANS.